(12) United States Patent
Roesicke et al.

(10) Patent No.: US 7,951,331 B2
(45) Date of Patent: May 31, 2011

(54) ANALYSIS SYSTEM AND METHOD FOR ANALYZING A SAMPLE ON AN ANALYTICAL TEST ELEMENT

(75) Inventors: Bernd Roesicke, Mannheim (DE); Stefan Kalveram, Viernheim (DE); Frederic Wehowski, Hockenheim (DE); Michael Goetz, Reichelsheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 992 days.

(21) Appl. No.: 11/776,379

(22) Filed: Jul. 11, 2007

(65) Prior Publication Data
US 2008/0053201 A1 Mar. 6, 2008

(30) Foreign Application Priority Data

Jul. 12, 2006 (EP) .................................. 06117020

(51) Int. Cl.
*G01N 21/00* (2006.01)
*G01N 15/06* (2006.01)
*G01J 1/48* (2006.01)
*G01N 35/00* (2006.01)
*G01N 27/26* (2006.01)

(52) U.S. Cl. ......... 422/68.1; 436/44; 436/164; 436/169; 436/170; 422/82.05; 422/87; 422/401; 422/404; 204/400; 204/403.02

(58) Field of Classification Search .................... None
See application file for complete search history.

(56) References Cited

U.S. PATENT DOCUMENTS

| | | | |
|---|---|---|---|
| 4,934,817 A * | 6/1990 | Gassenhuber | ............... 356/446 |
| 5,091,154 A | 2/1992 | Pauli et al. | |
| 5,313,721 A | 5/1994 | Filden | |
| 5,424,035 A | 6/1995 | Hones | |
| 5,489,414 A | 2/1996 | Schreiber et al. | |
| 5,846,837 A | 12/1998 | Thym et al. | |
| 5,904,898 A | 5/1999 | Markart | |
| 6,036,919 A | 3/2000 | Thym et al. | |
| 6,151,110 A * | 11/2000 | Markart | ....................... 356/244 |
| 6,707,554 B1 | 3/2004 | Miltner et al. | |
| 7,008,799 B1 | 3/2006 | Zimmer et al. | |

(Continued)

FOREIGN PATENT DOCUMENTS

DE 3921391 A1 1/1991
(Continued)

*Primary Examiner* — Jill Warden
*Assistant Examiner* — Neil Turk
(74) *Attorney, Agent, or Firm* — Justin L. Sage; Roche Diagnostics Operations, Inc.

(57) ABSTRACT

The invention relates to embodiments of an analysis system and to a method for analyzing a sample on an analytical test element, with the analysis system comprising a test element receptacle for receiving and positioning a test element in an analysis position. In an exemplary embodiment, the test element receptacle contains a guide part and a lock part, the guide part having means for guiding a test element into and out of the analysis position, the lock part comprising a frame and a bolt element, which frame and bolt element are connected to one another by a hinge. The bolt element can be pivoted about the hinge between a first position and a second position with respect to the frame. The bolt element comprises a latching lug for engaging in a recess in test element when the bolt element is in the first position and when the test element is positioned in the analysis position.

9 Claims, 1 Drawing Sheet

U.S. PATENT DOCUMENTS

| | | |
|---|---|---|
| 2002/0114735 A1 | 8/2002 | Markart |
| 2003/0157724 A1 | 8/2003 | Petrich et al. |
| 2005/0042765 A1 | 2/2005 | Hubner et al. |

FOREIGN PATENT DOCUMENTS

| | | |
|---|---|---|
| DE | 4328816 A1 | 3/1995 |
| DE | 19753847 A1 | 6/1999 |
| DE | 19822770 A1 | 11/1999 |
| EP | 0167661 A1 | 1/1986 |
| EP | 0376111 A2 | 7/1990 |
| EP | 0618443 A1 | 10/1994 |
| EP | 0645627 A1 | 3/1995 |
| EP | 0821233 A2 | 1/1998 |
| EP | 0821234 A2 | 1/1998 |
| EP | 0871033 A2 | 10/1998 |
| EP | 1508807 A2 | 2/2005 |
| WO | 97/02487 A1 | 1/1997 |
| WO | 00/19185 A1 | 4/2000 |
| WO | 01/48461 A1 | 7/2001 |

* cited by examiner

ANALYSIS SYSTEM AND METHOD FOR ANALYZING A SAMPLE ON AN ANALYTICAL TEST ELEMENT

REFERENCE TO RELATED APPLICATIONS

The present application is based on and claims priority to European Patent Application No. 06117020.5, filed Jul. 12, 2006, which is hereby incorporated by reference in its entirety.

BACKGROUND

The invention relates to an analysis system and to a method for analyzing a fluid sample on a test element, in particular for measuring the concentration of glucose in a body fluid on a test strip.

In order to analyze fluid samples, for example body fluids such as blood or urine, it is common to use analysis systems in which the samples to be analyzed are placed on a test element, typically interacting in a test field with one or more reagents on the test element before they are analyzed. The optical, e.g. photometric, and electromechanical evaluation of test elements are the most commonly used methods for rapidly determining the concentration of analyses in fluid samples. Analysis systems with test elements for fluid sample analysis are widely used in the fields of analysis, including environmental analysis as well as medical diagnosis. Test elements which are photometrically or electrochemically evaluated are of great value, particularly in the field of blood glucose diagnosis from capillary blood. Diagnostic test elements which are in the form of strips are referred to as test strips. The present invention relates to test elements of any desired shape, particularly to strip-like test elements.

For the analytical study of a fluid sample on a test element, analysis systems are known in the prior art which contain a test element receptacle for positioning the test element in a measurement position, and a measurement and evaluation device for carrying out a measurement and determining an analysis result based on this.

Primarily in the area of home-monitoring, that is to say where persons without specialist medical training carry out simple analyses of blood or of interstitial fluid themselves, such as diabetics taking blood samples on a regular basis, often several times a day, to monitor their blood glucose concentration, lancets and associated devices (so-called piercing aids) are sold that allow samples to be obtained with the least possible discomfort and in a reproducible manner.

In order to carry out the measurements, the sample is applied to an analytical test element which contains reagents (for example in a test field). When the reagents make contact with the sample, a reaction between the analyte contained in the sample and the reagents leads to a measurable change within the test element, this change correlating to the concentration of the analyte.

A measurement technique of the analysis system according to the invention is used to measure this change. The measured values obtained during the measurement method according to the measurement technique are used to determine the concentration of the analyte in the sample.

A suitable analysis system may be designed to carry out an electromechanical and/or photometric analysis. In photometric analysis systems, the test elements contain a reagent system whose reaction while the analyte leads to a photometrically detectable change (e.g. a change in color). In this case, the reagents are usually located in a test field of the test element, with the photometrics (e.g. color) of the reagents changing as a function of the concentration. This photometric change can be quantitatively determined, for example, by reflection photometry with the aid of a suitable measurement technique.

Electromechanical test elements contain an electromechanical reagent system in which one or more reactions with the analyte influence the electrical voltage applied between two poles of the test element and/or the current flowing between two poles of the test element at a defined voltage. As a result, the voltage or the current is therefore the measurable change which is determined by a suitable measurement technique, which is integrated in the analysis system and is designed as a voltage- or current-measuring device, and whose change, which correlates to the concentration of the analyte, is converted into analysis data (concentration of the analyte).

Many such known analysis systems are produced in complicated and costly manner from a large number of individually manufactured parts which then have to be assembled. In particular, the arrangements known from the prior art for positioning and locking test elements in an analysis position usually comprise a plurality of individual injection-moulded plastic parts and spring elements. The separate production processes and the assembly of the individual parts are costly and lead to more limiting tolerances in the basic positioning of the test element in the measurement and evaluation device. These parts usually correspond to the device housing structure, with the result that several interrelated tolerance factors have to be taken into account with respect to measurement accuracy, and this in turn leads to high costs on account of highly precise parts and processes.

The object of the invention is therefore to avoid the disadvantages of the prior art systems and, in particular, to provide an analysis system with cost-effective components, in particular with a cost-effective test element receptacle for positioning and locking a test element in an analysis position in the measurement and evaluation device.

BRIEF SUMMARY OF THE INVENTION

The object of the present invention is achieved in one embodiment by an analysis system for analyzing a sample on an analytical test element comprising a test element receptacle for receiving and positioning a test element in an analysis position, with the test element receptacle containing a guide part and a lock part. The guide part has means for guiding a test element into and out of the analysis position. The lock part comprises a frame and a bolt element, which frame and bolt element are connected to one another by means of a hinge. The bolt element can be pivoted about the hinge between a first position and a second position with respect to the frame. The bolt element comprises a latching lug for engaging a recess in a test element when the test element is positioned in the analysis position and the bolt element is in the first position.

The analysis system according to the invention is used for analyzing a fluid sample on an analytical test element. The sample is, for example, a body fluid such as blood or interstitial fluid. In clinical diagnostics, the examination of blood samples or of interstitial fluid permits early and reliable detection of pathological conditions and also specific and sound monitoring of physical states. Medical diagnostics also often entails obtaining a sample of blood or interstitial fluid from the individual who is to be examined.

To obtain the sample, a portion of the skin, for example on the finger pad or ear lobe, of the person to be examined is typically pierced with the aid of a sterile, sharp lancet in order to obtain a small amount of blood or interstitial fluid for the analysis. Embodiments of the present invention are particularly suitable for analysis of a sample which is carried out immediately after the sample has been obtained.

These and other features and advantages of the present invention will be more fully understood from the following detailed description of the present invention taken together with the accompanying claims. It is noted that the scope of the claims is definitely by the recitations therein and not by the specific discussion of the features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Figure 1:
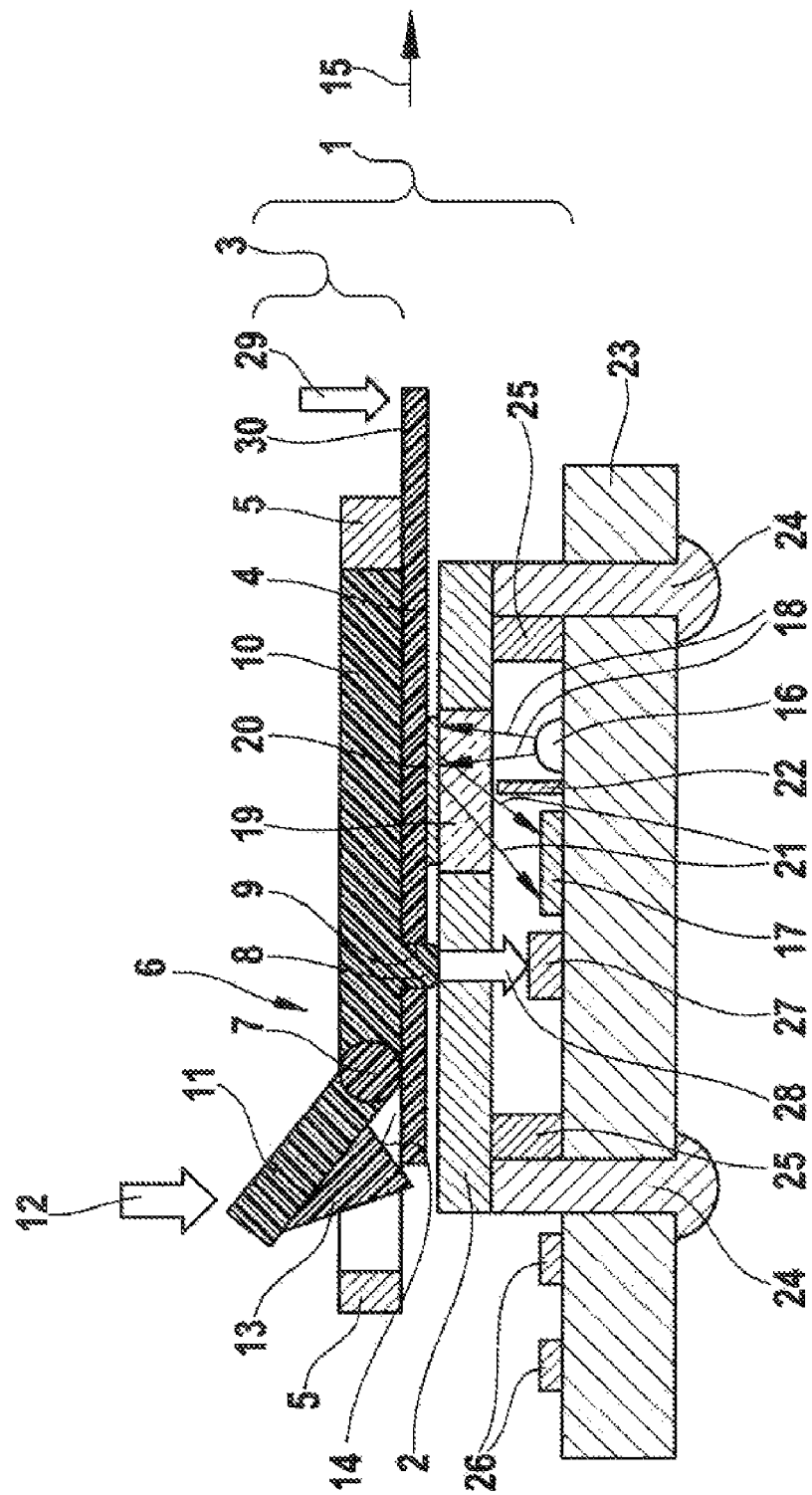
FIG. 1 is a cross sectional view of an analysis system according to the invention.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the present invention may be more readily understood, reference is made to the following examples, which are intended to illustrate the present invention, but not limited to the scope thereof.

DETAILED DESCRIPTION OF EMBODIMENTS OF THE PRESENT INVENTION

The following description of the preferred embodiment is merely exemplary in nature and is in no way intended to limit the present invention or its application or uses.

The analysis system according to one embodiment of the present invention comprises a test element receptacle configured for receiving and positioning a test element in an analysis position. In this case, the analysis position is that position of the test element within the analysis system in which the sample is analyzed on the test element by a measurement and evaluation device. The positioning of the test elements in the analysis system is of great importance both for the accuracy of the analysis and for ease of handling. One objective when carrying out analytical tests is to reduce the amount of sample required to be used or to carry out reliable analysis even when only small amounts of sample are available. In the field of blood glucose analysis, a drop of blood has to be taken from a body part of a person, the said person being more comfortable if the amount of blood required for the test is as low as possible. The reduction in the amount of sample is associated with a reduction in the size of the test elements and in particular the detection zones located on the test elements. In order to ensure accurate analysis of the sample, it is necessary to precisely position the detection zone in the analysis system. In photometric analysis systems, for example, incorrect physical orientation of the test element leads directly to a reduction in the size of the effective measurement area for detecting photometric changes, and as a result can lead to a measurement error.

In certain embodiments of the present invention, the analysis system has a slot in its housing for manually inserting a test element into the test element receptacle. However, the test element can also be pushed into the test element receptacle automatically, for example by a tappet which is moved by means of a drive unit after the test element has been automatically removed from a test element magazine. In any event, the test element slides into the analysis position guided by means for guiding the test element in a guide part of the test element receptacle. The means for guiding the test element are, for example, a lower support face and two lateral guide faces which guide the test element as if in a channel. The guiding means can also be, for example, lateral grooves which are provided in the interior of the guide part and into which the two longitudinal edges of the test element engage, or a plurality of lateral projections on which the longitudinal edges of the test element rest.

In the analysis position, a lock part serves to "lock" or otherwise fix or hold the test element so that it is held in the position intended for analysis. Locking prevents the test element from being unintentionally drawn back or falling out during the measurement process. In one embodiment, the lock part comprises a frame and a bolt element. The frame serves, for example, to connect the lock part to the guide part. The bolt element is connected to the frame by means of a hinge. In other embodiments, the frame, hinge and bolt element are integrally formed. In embodiments in which the bolt element and hinge are integrally formed, the hinge may comprise a film hinge. Film hinges (or film joints) are strip-like hinges and do not have any additional mechanical parts. Film hinges are known in the plastics industry and are used to enable two parts to pivot relative to one another without the hinge comprising bolts or eyelets. One example in the prior art of a suitable film hinge for use in embodiments of the lock part can be found in U.S. Pat. No. 5,313,721 in which a clip for attaching an ID pass has a film hinge. Throughout the remaining disclosure, reference will largely be made to using the film hinge, although suitable alternative structures for a film hinge will be apparent to persons of ordinary skill in the art in the view of the present disclosure.

In embodiments of the present invention, the bolt element can be pivoted about the hinge between a first position and a second position with respect to the frame. Typically this is caused by the action of an external force on the bolt element. When the bolt element is pivoted into the second position, the hinge, e.g. a film hinge, is typically elastically deformed by torsion, with the deformation energy being released again when the load on the film hinge is removed and the bolt element biasedly pivots back into the first position. In such embodiments, the deformed film hinge in the second position consequently generates a defined restoring force which pivots the bolt element back in the direction of the first position as soon as an external force ceases to act against this restoring force. That is, the bolt element is biased to the first position. The magnitude of the restoring force generated in this way is determined, inter alia, by the material and the shape of the film hinge as well as the pre-stressed (biased) position in which the bolt element is configured. The use of a film hinge in the analysis system according to the invention therefore obviates the need for a spring element or other biasing structure in order to keep the bolt element in the first (basic) position and to pivot the bolt element from the second position back into the first (basic) position again. Clearly, however, other hinge configurations are possible that may provide suitable biasing and restoring forces, including spring biased hinges, which may have more parts and resulting manufacturing tolerances than a simple, prestressable film hinge.

In embodiments of the present invention, the bolt element further comprises a latching lug which can engage a recess provided in a test element when it is positioned in the analysis position and locks it there. When the latching lug is engaged in the recess, the bolt element is typically located in the first position or at least pivoted out of the second position in the general direction of the first position. The recess in the test element may be an opening which runs through the entire thickness of the test element from one side to the other, or a depression having a depth corresponding to only a part of the thickness of the test element.

In use, when the test element receptacle is empty, the bolt element in one embodiment rests in the first position. As a test element is inserted into the test element receptacle, the bolt element is deformed slightly into the second position, with the latching lug sliding over the surface of the test element. When the test element reaches the analysis position, the latching lug engages the recess, and the bolt element pivots back in the general direction of the first position. In embodiments in which the test element is manually inserted into the test element receptacle, the latching operation can be arranged to produce a perceptible, tactile feedback for the user when the test element reaches the analysis position and engages with the latching lug. To remove the test element, the lock has to be released. The latching lug is pivoted out of the recess into the second position by application of a force on the bolt element to deform the film hinge. If there is no test element in the test element receptacle, the bolt element preferentially rests in the first position.

The present invention also relates to a method for analyzing a sample on an analytical test element in an analysis system, comprising the steps of receiving a test element in a test element receptacle of the analysis system, with the test element being guided into an analysis position by means for guiding the test element in a guide part of the test element receptacle, and the test element being locked in the analysis position by the lock part of the test element receptacle, which has a frame and a bolt element which are connected to one another by means of a hinge, by the bolt element pivoting about the hinge out of a second position into a first position in which a latching lug of the bolt element engages in a recess in the test element which is positioned in the analysis position; and analyzing the sample in a test field of the test element using a measurement technique of the analysis system.

The analysis system according to the invention is suitable for carrying out the method according to the invention.

According to one embodiment of the present invention, the lock part and the guide part are two injection-moulded plastic parts. In such embodiment, the two parts can be produced using a single-compound injection-molding process. However, multi-component injection moulding is also possible (for example production of the frame, the film hinge and/or the bolt element from different materials). In other embodiments, the lock part is covered by a cover (for example a cap) in the analysis system, the cover permitting an (indirect) external force to be exerted on the bolt element in order to pivot the bolt element into the second position (with the cap being pivoted relative to the frame and to the guide part together with the bolt element). In such embodiments, it is possible to use the cover to protect the lock part against the ingress of dirt, to enable a user to operate the bolt element in a manner which is comfortable from a tactile point of view, and also to create an appealing design. The cover can also be removed from the lock part in order to permit the lock part to be cleaned. The cover, the frame and the bolt element can furthermore be removed from the guide part in order to enable the guide part, and possibly the parts removed from it, to be cleaned.

Injection molding is a process which is known in the prior art and in which a plasticized material (injection-moulding compound such as a thermoplastic or thermosetting material) is injected into a forming die (injection-moulding die) under high pressure and there assumes the solid state under the action of pressure. The injection-moulded part can then be removed from the injection-moulding die. Multi-component injection moulding is also a method which is known from the prior art. So-called composite injection moulding is suitable, for example, for producing multi-component injection-moulded subassemblies for the analysis system according to the invention. In this case, two or more materials are injected into an injection-moulding die one after the other, as a result of which their boundary areas form a material connection with one another. The geometry of the cavity present in the injection-moulding die is changed between the various injection operations.

In embodiments of the invention in which the hinge comprises a film hinge, the film hinge can be, for example, injection-molded from polypropylene. This material has the requisite suppleness and extensibility for long-term operation of the film hinge. Further possible materials for producing film hinges include polyethylene, ethylene/vinyl acetate or polyamides.

According to one embodiment of the present invention, the test element receptacle can be at least partially removed from the analysis system. Furthermore, the lock part (in particular the frame) may be releasably connected to the guide part. On account of the ability to remove the test element receptacle or at least part of the said test element receptacle and/or the releasable connection between the lock part and guide part, it is possible in such embodiments to clean the areas in the analysis system which come into contact with the test element, in particular in order to remove sample residues from these areas. Embodiments for a feasible releasable connection between the test element receptacle and the analysis system and/or between the lock part and the guide part include, without limitation, a plug-in connection, a snap-action connection, a latching connection or a clip connection. Typically, however, the test element receptacle is designed such that the areas of the test element which are wetted by the sample do not come into contact with the surfaces of the lock part and of the guide part, and soiling of the parts is therefore kept low.

According to another embodiment of the present invention, the bolt element is prestressed (or biased) in the first position. In the absence of the test element, the bolt element is thus held under prestress in a defined rest position, in particular against the support face for the test element in the guide part. The test element is then inserted against a certain resistance since the bolt element is raised by the test element against the prestress and slides over the surface of the test element. Upon reaching the recess in the test element, the latching lug of the bolt element automatically latches into the said recess by virtue of the prestress and fixes the test element in the analysis position.

According to yet another embodiment of the present invention, the bolt element comprises a lever configured to rotate about the hinge, having a first lever arm and a second lever arm, with the first lever arm having the latching lug. A force applied to the second lever arm allows a user to pivot the bolt element out of the first position into the second position. By way of example, the film hinge can be arranged in the middle of the bolt element, with the result that the bolt element comprises two lever arms of equal length. In other embodiments, the lever arms are preferably arranged in an inflexible manner in relation to one another, with the result that their position relative to one another does not change when the bolt element is pivoted. The two lever arms can have a common longitudinal axis ($\alpha=180°$) or can be arranged at an angle of $\alpha<180°$ in relation to one another. In use, if the user of the analysis system according to the invention presses the second lever arm, the bolt element resultingly pivots about the film hinge relative to the frame, and the first level arm with the latching lug is pivoted out of its location in the first position of the bolt element into its location in the second position of the bolt element. A particular result of this is that the latching lug is moved out of engagement in a recess of a test element in the analysis position and the test element is therefore released for the purpose of removal from the test element receptacle.

In yet other embodiments, the second lever arm comprises a pushing element configured to exert a pushing force on a test element positioned in the analysis position, in a discharge direction when the bolt element is pivoted out of the first position into the second position. In this case, the discharge direction is that direction in which the test element receptacle discharges the unlocked test element (for example for disposal purposes after a sample analysis has been performed). In such an embodiment, the test element and the ejection mechanism are latched by means of a single component in the analysis system (namely the bolt element). The pushing force of the pushing element can also have a releasing effect on the test element in order to loosen the test element in the event it may possibly be stuck in the test element receptacle on account of sample residues (for example blood residues), after which the test element can then be removed from the test element receptacle, for example by being manually withdrawn or by being shaken out. The pushing force can also cause the test element to be at least partially automatically pushed out of the test element receptacle.

The invention also relates to a method for analyzing a sample on an analytical test element, in which method, for the purpose of removing the test element from the test element receptacle of the analysis system, the bolt element is pivoted into the second position and in the process the latching lug is automatically moved out of the recess in the test element at the same time, and a pushing element, which is provided on the bolt element, exerts a force on the test element, which is positioned in the analysis position, in a discharge direction.

According to one embodiment of the present invention, the analysis system contains a measurement technique for the photometric analysis of a sample on an analytical test element which is located in an analysis position in the test element receptacle of the analysis system. Such an analysis system typically comprises a measurement technique with at least one light source and at least one detector. The light source and the detector are arranged such that light from the light source can pass through a light-transmissive region of the guide part to a test field of a test element which is arranged in the analysis position and, in a reflected manner, from the test field through the light-transmissive region to the detector. The light-transmissive region is, for example, a window which is open or is filled with a light-transmissive material, a diaphragm, a lens or any desired combination of these elements. The light source is, for example, a light-emitting device (LED). The guide part and the lock part ensure accurate positioning of the test field relative to the light source and the detector during the measurement operation.

During the measurement method, the test element is positioned in the test element receptacle such that the light from the light source is directed onto a test field, which contains the sample and the reagents, on the test element via the light-transmissive region of the guide part. Depending on the concentration of the analyte in the sample, a proportion of the light which strikes the test element is reflected at this test element such that it passes through the light-transmissive region of the guide part to the detector. The detector is, for example, a photodiode. The light source and the detector are typically screened from one another by a screening means (for example a diaphragm) such that direct radiation of light from the light source onto the detector is largely prevented.

The photometric measurement technique of the analysis system according to embodiments of the present invention typically does not contain any optical lenses, but only optical diaphragms. A measurement technique of this type is more cost-effective than a measurement technique containing optical lenses, and the tolerance sensitivity of the measurement technique is reduced.

In an analysis system according to certain embodiments of the invention comprising a photometric measurement technique, the bolt element is configured for (a) fixing the test element in the analysis position; (b) providing the tactile feedback to the user when the test element reaches the analysis position; (c) optically screening the measurement technique against external light; and (d) releasing the test element in the event of removal.

According to one embodiment of the present invention comprising a photometric measurement technique, the light source and the detector are arranged on a printed circuit board on which the guide part is fixed, with at least one spacer being arranged between the printed circuit board and the guide part. In this case, the printed circuit board contains conductor tracks by means of which the light source and the detector are supplied with electrical voltage. The spacer keeps the guide part and the printed circuit board at a defined distance from one another and therefore also keeps the light source detector arrangement at a defined distance from the guide part. Consequently, a test element which is inserted into the guide part as far as the analysis position is held in a defined position relative to the measurement technique in order to ensure specific measurement conditions.

In other embodiments, the analysis system according to the invention contains a switch which interacts with the latching lug of the bolt element such that the switch is operated by the latching lug in the first position of the bolt element. The analysis system uses this switch to detect when a test element is positioned in the analysis position. The switch serves to electrically indicate the positioning of the test element. As a result, a signal for switching on the analysis system or a start signal for starting a measurement operation can, for example, be triggered. The starting process is therefore not dependent on the longitudinal tolerances of the test element or on switching hystereses. In order to trigger a start signal, the switching logic can, for example, be detected, with the result that starting is only permitted when the bolt element moves from the second position to the first position before a measurement operation.

According to the further embodiment of the present invention, an optical scanning apparatus is provided which is configured to scan the test element along one surface when the test element is received in the test element receptacle. Given appropriate design of the surface profile, for example by dark and light fields which produce a defined course of a reflection measurement operation when the test element is inserted, it is possible, for example, to detect that insertion of a test element into the guide part has started and/or that the test element has reached the analysis position. As a result, signals for switching on the analysis system and/or for starting the measurement process can be triggered. The detected light which is reflected through the surface of the test element can also be used to determine a correction value or to provide calibration information for a subsequent measurement operation by the provided measurement technique of the analysis system. In addition, a switch which can be operated by the latching lug of the bolt element can be provided in this embodiment. However, the switch can also be dispensed with.

The present invention also relates to the use of an analysis system according to the invention for measuring for concentration of glucose in a body fluid on a test strip. The test strip is typically a capillary channel test element in which the sample (for example blood from the finger pad) is passed to the capillary channel and supplied to the detection zone (the test field) through the said capillary channel. However, it is also possible to use a test strip in which the sample is placed directly on the detection zone and the test strip is then inserted into the test element receptacle.

Referring to the embodiment of the invention illustrated in FIG. 1, a test element receptacle 1 is provided which contains a guide part 2 and a lock part 3. The guide part 2 serves to guide a test element 4 as it is inserted into and removed from the test element receptacle 1. To this end, the guide part 2 has means for guiding the test element 4, e.g. in the form of lateral guide faces and a support face (not illustrated). The lock part 3 has a frame 5 and a bolt element 6. The bolt element 6 is a bar which is integrally connected to the frame 5 by means of a film hinge 7. The bolt element 6 can be pivoted about the film hinge 7 between a first position and a second position with respect to the frame 5, which resultingly deforms the film hinge 7. FIG. 1 illustrates the bolt element 6 in a first position. The bolt element 6 has a latching lug 8 which, in this first position of the bolt element 6, engages in a recess 9 in the test element 4 which is positioned in the analysis position. The test element 4 is therefore locked in the analysis position by the bolt element 6. The bolt element 6 is typically pre-stressed in this position.

The bolt element 6 according to FIG. 1 is a lever, which can rotate about the film hinge 7, having a first lever arm 10 and a second lever arm 11. The first lever arm 10 is provided with the latching lug 8. The second lever arm 11 is arranged at an angle $\alpha < 180°$ ($\alpha \cong 135°$) relative to the first lever arm 10. The bolt element 6 can be pivoted out of the first portion into a second position (not illustrated) by virtue of the action of force 12 on the second lever arm 11, in which second position the latching lug 8 no longer engages in the recess 9 in the test element 4, and the test element 4 is therefore unlocked.

The second lever arm 11 contains a pushing element 13 which uses the pushing face 14 to exert a pushing force and/or a releasing moment on the test element 4 in the discharge direction 15 when the bolt element 6 is pivoted out of the first position into the second position (on account of the action of force 12). As a result, the test element 4 is released from the analysis position and can be withdrawn from the test element receptacle in the discharge direction 15 and disposed of by a user.

FIG. 1 also illustrates this embodiment of the present invention in the context of a system using a photometric measurement technique. Such an analysis system typically comprises a light source 16 (LED) and a detector 17 (photodiode). The light source 16 and the detector 17 are arranged such that the light 18 radiated by the light source 16 can pass through a light-transmissive region 19 of the guide part 2 to the test field 20 of the test element 4 which is arranged in the analysis position. The light-transmissive region 19 is an aperture which is filled by a plastic window. The light 21 which is reflected at the test field 20 again passes through the light-transmissive region 19 to the detector 17, with a streaming means 22 separating the radiated light 18 from the reflected light 21. The light source 16 and the detector 17 are arranged on a printed circuit board 23 on which the guide part 2 is fixed by means of fixing elements 24, with spacers 25 being arranged between the printed circuit board 23 and the guide part 2. The printed circuit board 23 is also fitted with further subassemblies 26 of the analysis system.

A switch 27 is also arranged on the printed circuit board 23, the said switch interacting with the latching lug 8 by means of a switching tappet 28 in such a way that the said switch is operated by the latching lug 8 by means of the switching tappet 28 in the first position of the bolt element 6 (which is illustrated in FIG. 1).

In order to carry out a measurement method using the analysis system, a sample is placed 29 on one end 30 of the test element 4 when the test element is positioned in the analysis position. End 30 typically projects out of the test element receptacle when the test element is in the analysis position. From end 30, the sample (for example a drop of blood) is transported to the test field 20, typically by means of a capillary (not illustrated). As noted above, the illustrated analysis system performs a photometric measurement operation in order to determine the concentration of an analyte in the sample. Other embodiments of the present invention may be provided in a system using an electromechanical measurement technique and method, for which appropriate chemical, electrical and connective structures are provided on the test element and the receptacle, which are known in the field of fluid analysis system.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purpose of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present invention in detail and by reference to specific embodiments thereof, it will be apparent that modification and variations are possible without departing from the scope of the present invention defined n the appended claims. More specifically, although some aspects of the present invention are identified herein as preferred or particularly advantageous, it is contemplated that the present invention is not necessarily limited to these preferred aspects of the present invention.

What is claimed is:

1. Analysis system for analyzing a sample on an analytical test element, comprising a measurement and evaluation device configured for analyzing a sample using a test element, the device comprising a test element receptacle configured for receiving and positioning the test element in an analysis position, the test element receptacle comprising a guide part and a lock part, the guide part being configured to guide the test element into and out of the analysis position, the lock part comprising a frame and a bolt element, the frame and bolt element being integrally connected to one another by a film hinge, the bolt element being pivotable about the film hinge in order to move between a first position and a second position relative to the frame, the bolt element comprising a latching lug for engaging a recess provided in the test element when the test element is positioned in the analysis position and when the bolt element is in the first position, the bolt element further comprising a lever having a first lever arm and a second lever arm pivotally connected by the film hinge, the first lever arm having the latching lug, the bolt element being pivotable between the first position and the second position by application of a force on the second lever arm, wherein the second lever arm comprises a pushing element configured to exert a pushing force in a discharge direction on the test element when positioned in the analysis position when the bolt element is pivoted from the first position into the second position.

2. Analysis system according to claim 1, wherein the lock part and the guide part are injection-molded plastic parts.

3. Analysis system according to claim 1, wherein the lock part is releasably connected to the guide part.

4. Analysis system according to claim 1, wherein the bolt element is prestressed in the first position.

5. Analysis system according to claim 1, the system being configured to operate according to a photometric measurement technique, the system further comprising a light source and a detector arranged relative to each other such that light from the light source is able to pass through a light-transmissive region provided in the guide part to a test field provided on the test element when the test element is in the analysis position, the light further passing in a reflected manner from the test field through the light-transmissive region to the detector.

6. Analysis system according to claim 5, wherein the light source and the detector are arranged on a printed circuit board on which the guide part is fixed, at least one spacer being arranged between the printed circuit board and the guide part.

7. Analysis system according to claim 1, further comprising a switch configured to interact with the latching lug of the bolt element to electrically indicate the positioning of the test element, wherein the switch is triggered by the engagement of the latching lug with the recess when the test element is in the analysis position and the bolt element is in the first position.

8. Method for analysis of a sample on an analytical test element in an analysis system, the analysis system comprising a measurement and evaluation device configured for analyzing a sample applied to a test field on the test element according to a measurement technique, the method comprising the steps of:
   receiving a test element in a test element receptacle of the analysis system, the test element being guided into an analysis position by means for guiding the test element in a guide part of the test element receptacle, the test element being locked in the analysis position by a lock part of the test element receptacle, the lock part having a frame and a bolt element which are connected to one another by means of a hinge, the bolt element pivoting about the hinge between a second position and a first position in which a latching lug of the bolt element engages in a recess in the test element which is positioned in the analysis position,
   applying a sample to the test field of the test element positioned in the analysis position,
   analyzing the sample in a test field of the test element using the measurement technique of the analysis system and
   removing the test element from the test element receptacle by pivoting the bolt element into the second position to cause the latching lug to disengage from the recess in the test element, and exerting a force on the test element in a discharge direction, the force being provided by a pushing element provided on the bolt element when the bolt element is moved from the first position to the second position.

9. Method according to claim 8, further comprising the step of scanning the test element along one surface when the test element is received in the test element receptacle, using an optical scanning apparatus provided in the analysis system.

\* \* \* \* \*